United States Patent
Westlund et al.

(10) Patent No.: US 7,966,076 B2
(45) Date of Patent: Jun. 21, 2011

(54) LEAD AND APPARATUS FOR STIMULATION OF THE CARDIAC PLEXUS

(75) Inventors: Randy W. Westlund, River Falls, WI (US); Anthony V. Caparso, St. Louis Park, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 291 days.

(21) Appl. No.: 11/685,511

(22) Filed: Mar. 13, 2007

(65) Prior Publication Data
US 2008/0228252 A1    Sep. 18, 2008

(51) Int. Cl.
*A61N 1/05* (2006.01)
(52) U.S. Cl. .................... 607/130; 607/119
(58) Field of Classification Search ............. 607/130
See application file for complete search history.

(56) References Cited

U.S. PATENT DOCUMENTS

| | | | |
|---|---|---|---|
| 4,177,818 A * | 12/1979 | De Pedro | 607/130 |
| 5,215,089 A | 6/1993 | Baker, Jr. | |
| 5,846,196 A * | 12/1998 | Siekmeyer et al. | 600/374 |
| 6,205,361 B1 * | 3/2001 | Kuzma et al. | 607/116 |
| 6,937,896 B1 | 8/2005 | Kroll | |
| 7,146,221 B2 * | 12/2006 | Krulevitch et al. | 607/116 |
| 7,277,761 B2 * | 10/2007 | Shelchuk | 607/62 |
| 2003/0229380 A1 * | 12/2003 | Adams et al. | 607/9 |
| 2004/0049235 A1 | 3/2004 | Deno et al. | |
| 2004/0064158 A1 * | 4/2004 | Klein et al. | 607/9 |
| 2004/0186532 A1 | 9/2004 | Tadlock | |
| 2004/0249416 A1 | 12/2004 | Yun et al. | |
| 2006/0161238 A1 * | 7/2006 | Hall | 607/129 |
| 2007/0027496 A1 | 2/2007 | Parnis et al. | |
| 2007/0191902 A1 | 8/2007 | Errico et al. | |

OTHER PUBLICATIONS

International Search Report and Written Opinion of international application No. PCT/US2008/051692, mailed Jun. 9, 2008, 15 pp.

* cited by examiner

*Primary Examiner* — Carl H Layno
*Assistant Examiner* — Jeremiah T Kimball
(74) *Attorney, Agent, or Firm* — Faegre & Benson LLP

(57) ABSTRACT

A medical electrical lead adapted to stimulate a patient's cardiac plexus includes a flexible distal portion having a surface adapted to conform to an outer surface of an aortic region generally associated with the cardiac plexus. The distal portion can have one or more elongate members. Alternatively, the distal portion can have a generally planar portion. The distal portion is flexible such that it can be furled or otherwise compacted such that it can be delivered to a target stimulation site using a guide catheter or other delivery tool, such as a cannula.

4 Claims, 9 Drawing Sheets

US 7,966,076 B2

LEAD AND APPARATUS FOR STIMULATION OF THE CARDIAC PLEXUS

TECHNICAL FIELD

The present invention generally relates to an implantable lead for selectively stimulating the autonomic nervous system. More particularly the present invention relates to an implantable lead for stimulating the autonomic nervous system from a location adjacent the cardiac plexus and/or coronary plexuses.

BACKGROUND

The autonomic nervous system includes the sympathetic and parasympathetic pathways. Stimulation of nerves in these pathways affects cardiac operation and/or function. In general, stimulation of the sympathetic nerves causes an increase in heart rate and inotropy (contractility) and hence cardiac output. In contrast, stimulation of the parasympathetic nerves generally causes a decrease in atrial rate and contractile force, atrio-ventricular nodal conduction, and ventricular contractile force. Hence, selective stimulation of the autonomic nerves can provide a means for cardiac control for the purpose of modulating cardiac electrophysiology and/or cardiac hemodynamics.

The functions associated with the sympathetic and parasympathetic nervous systems are many and can be complexly integrated with each other. Thus, an indiscriminate stimulation of the sympathetic and/or parasympathetic nervous system to achieve a desired response in one physiological system may also result in an undesired response in other physiological systems. The cardiac plexus provides an alternative location within a patient's anatomy for selectively stimulating a portion of a patient's autonomic nervous system.

Thus, a need exists for an implantable lead including an electrode array capable of selectively and chronically stimulating the sympathetic and parasympathetic nervous system from an alternative site such as the cardiac plexus.

SUMMARY

According to one embodiment of the present invention, a medical electrical lead includes: a proximal portion including a proximal end adapted to be connected to a pulse generator; a flexible distal portion adapted to conform to an aortic region generally associated with a cardiac plexus; and a plurality of electrodes located on the one or more elongate members, the electrodes adapted to deliver an electrical pulse to the cardiac plexus.

The present invention is also directed to a method of implanting a lead adapted for stimulating a patient's cardiac plexus. According to one embodiment of the present invention, the method includes providing a lead having a flexible distal portion having a generally planar surface adapted to conform to an outer surface of a patient's aortic arch at a location generally associated with the cardiac plexus. The lead includes at least one fixation member adapted to engage the outer surface of the aortic arch and at least two electrodes adapted to deliver an electrical pulse to the cardiac plexus. Additionally, the method includes establishing an access port in a thoracic region of a patient's body; delivering the lead through the port to the aortic arch at the location generally associated with the cardiac plexus; anchoring the distal portion cardiac plexus; and chronically stimulating the cardiac plexus.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1A:
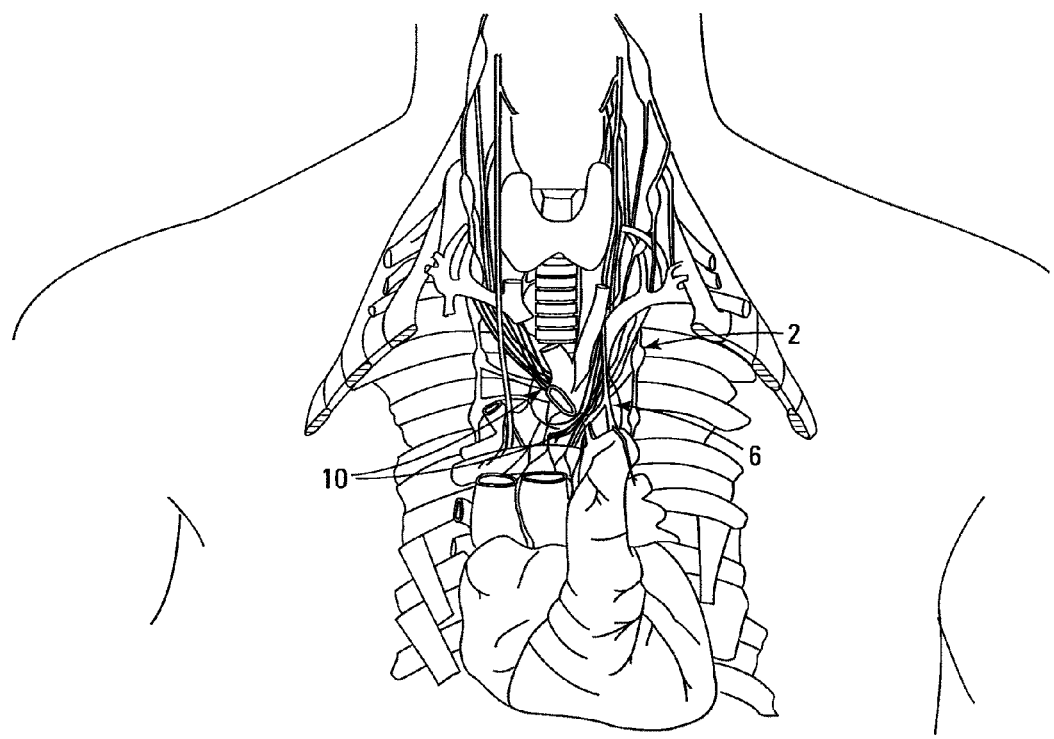
FIG. 1A is a schematic view of the upper portion of a patient's autonomic nervous system.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1B:
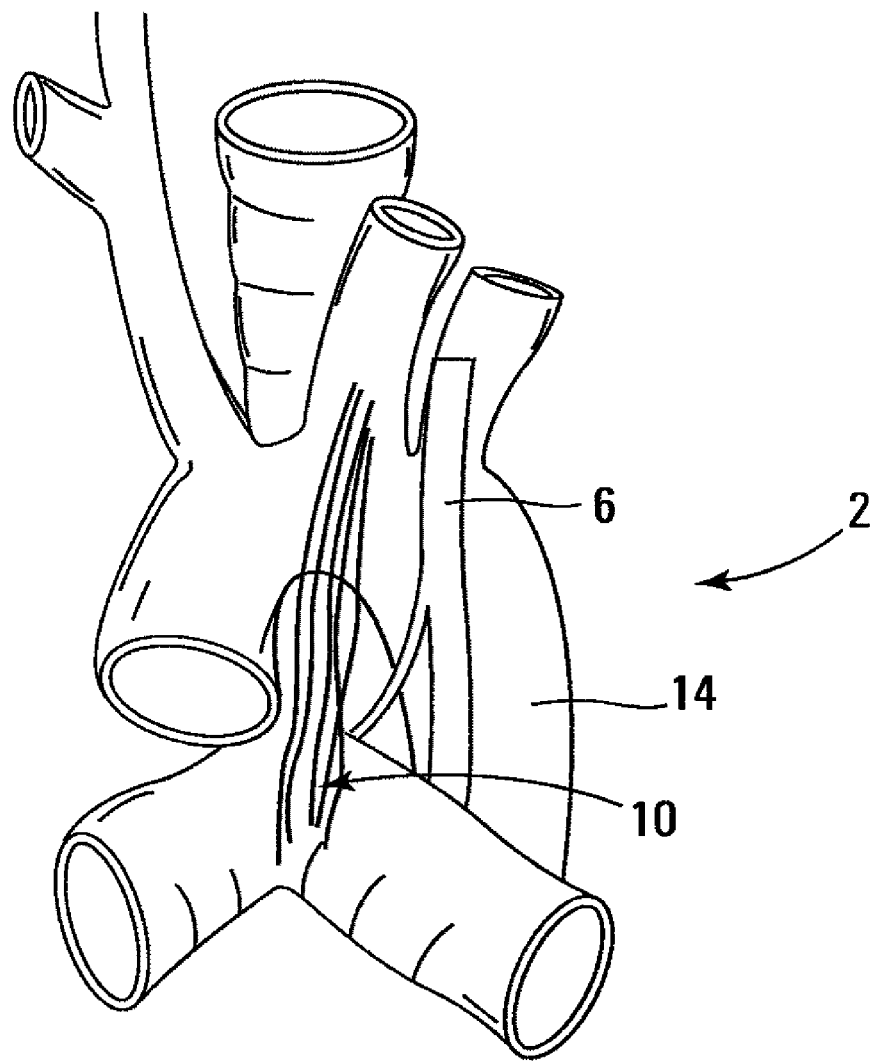
FIG. 1B is a close-up, partial anterior view of the upper portion of a patient's autonomic nervous system showing the left vagus nerve and the cardiac plexus.

FIG. 1 is a schematic view of a portion of a patient's autonomic nervous system 2. FIG. 1B is a close-up, partial anterior view of the upper portion of a patient's autonomic nervous system 2 showing the left vagus nerve 6 and the superficial cardiac plexus 10.

The cardiac plexus 10 is comprised of an anterior (superficial) and posterior (deep) plexus. The anterior plexus lies beneath the arch of the aorta and in front of the right pulmonary artery. The posterior plexus lies in front of the trachea and behind the aortic arch. Both plexuses are formed by the convergence of the cardiac sympathetic nerves that arise from the sympathetic trunk and cardiac parasympathetic nerves that branch from the vagus and recurrent laryngeal nerves.

Figure 2A:
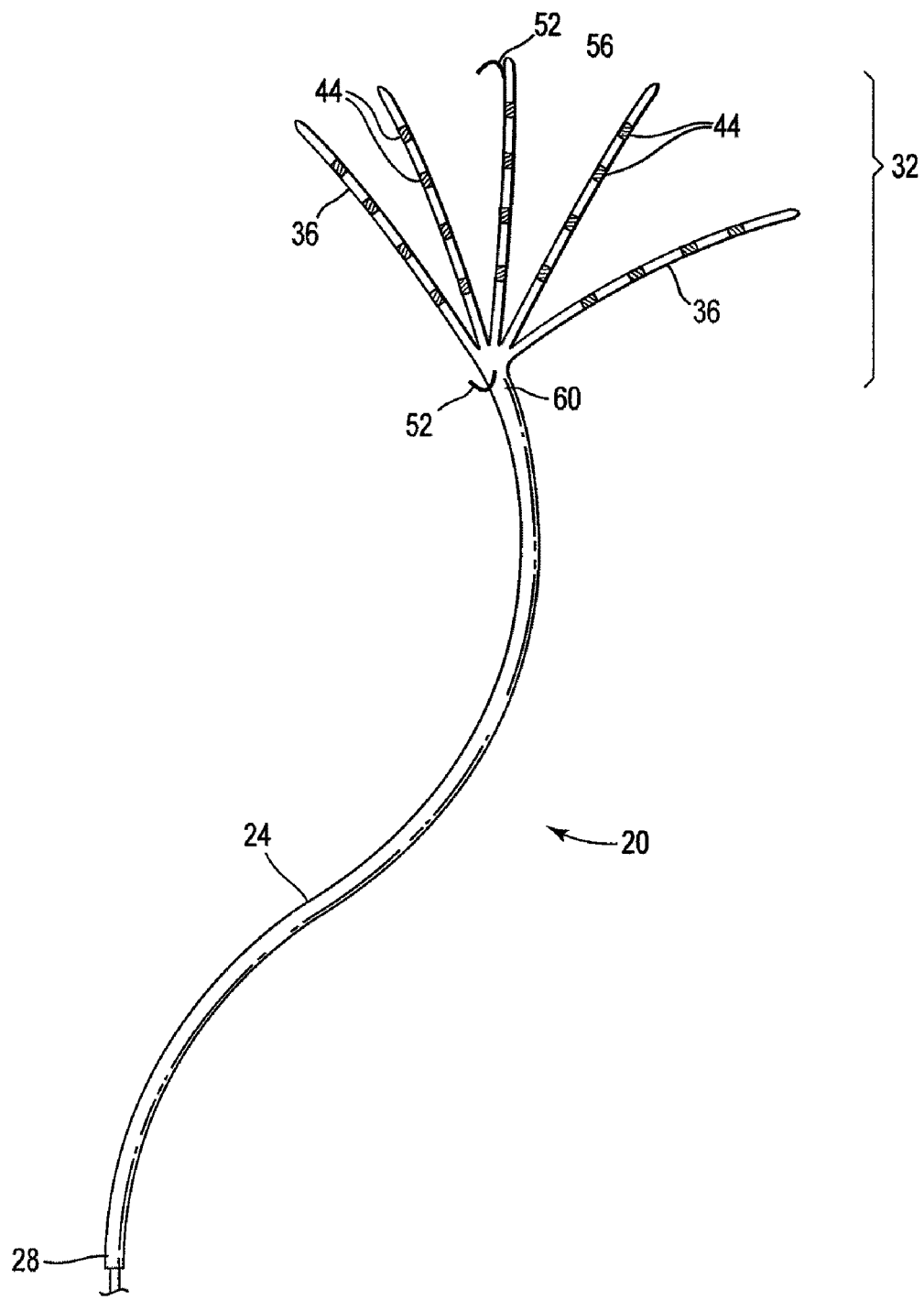
FIGS. 2A and 2B are schematic views of a lead according to various embodiments of the present invention.
Figure 2B:
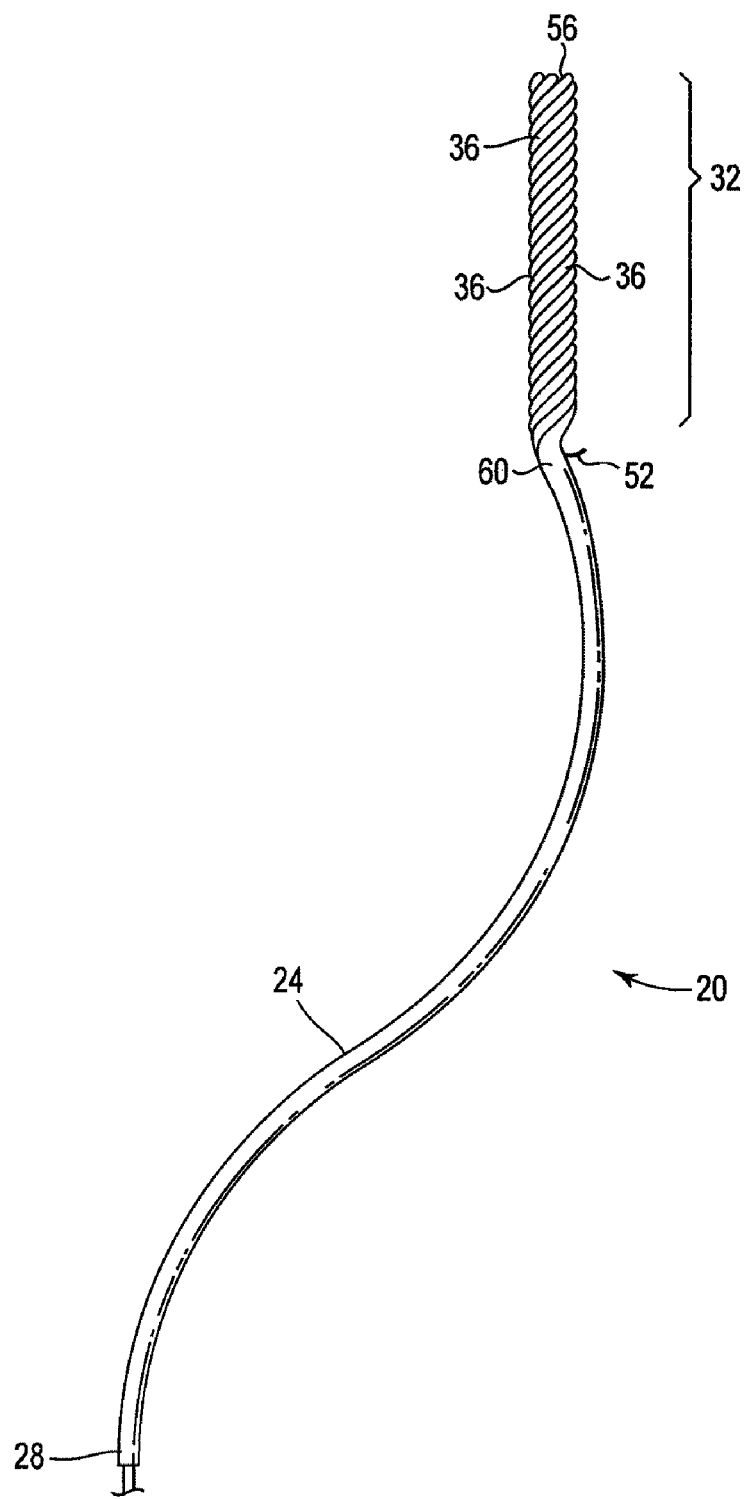
Figure 3A:
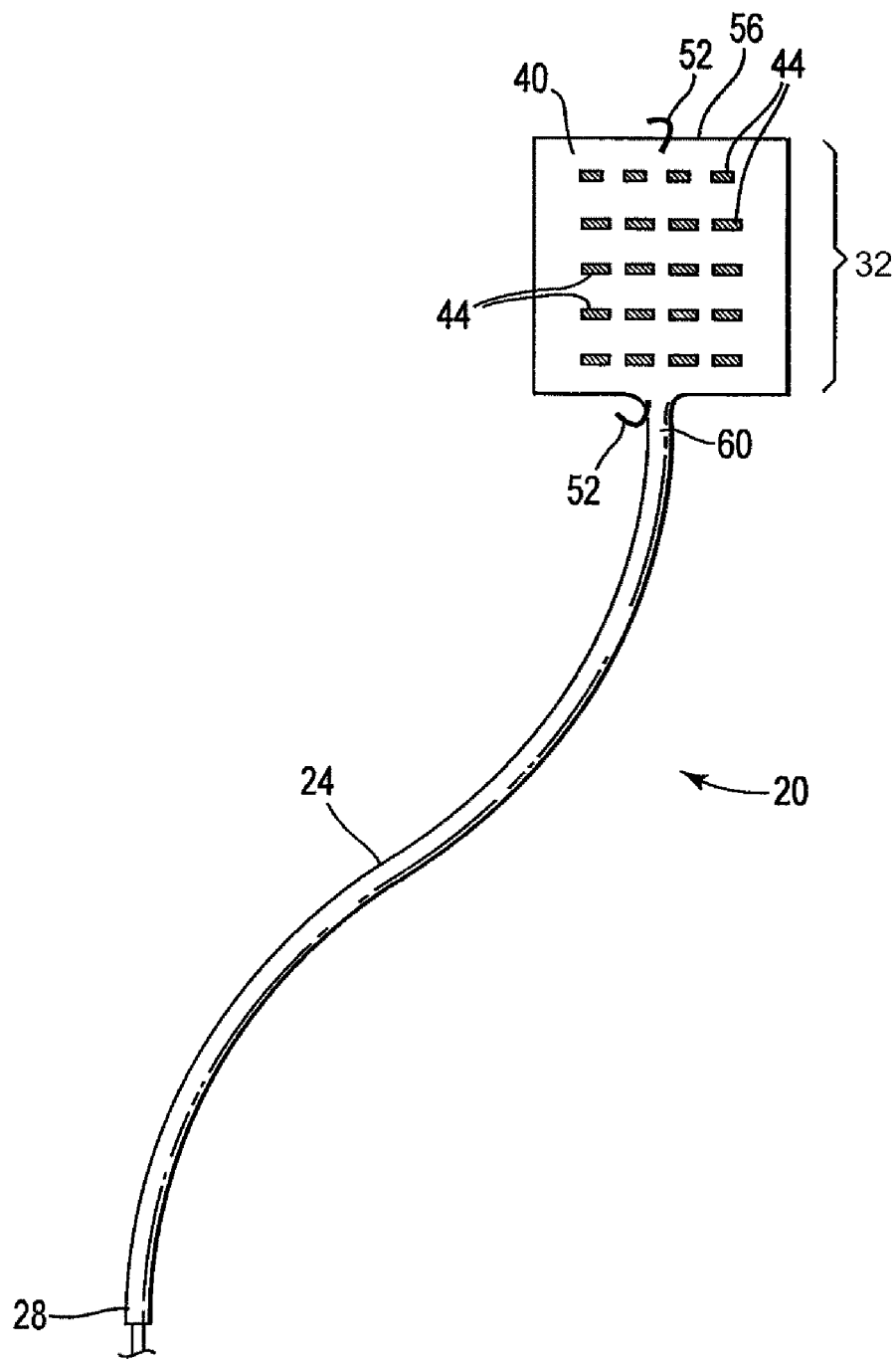
FIGS. 3A and 3B are schematic views of a lead according to other embodiments of the present invention
Figure 3B:
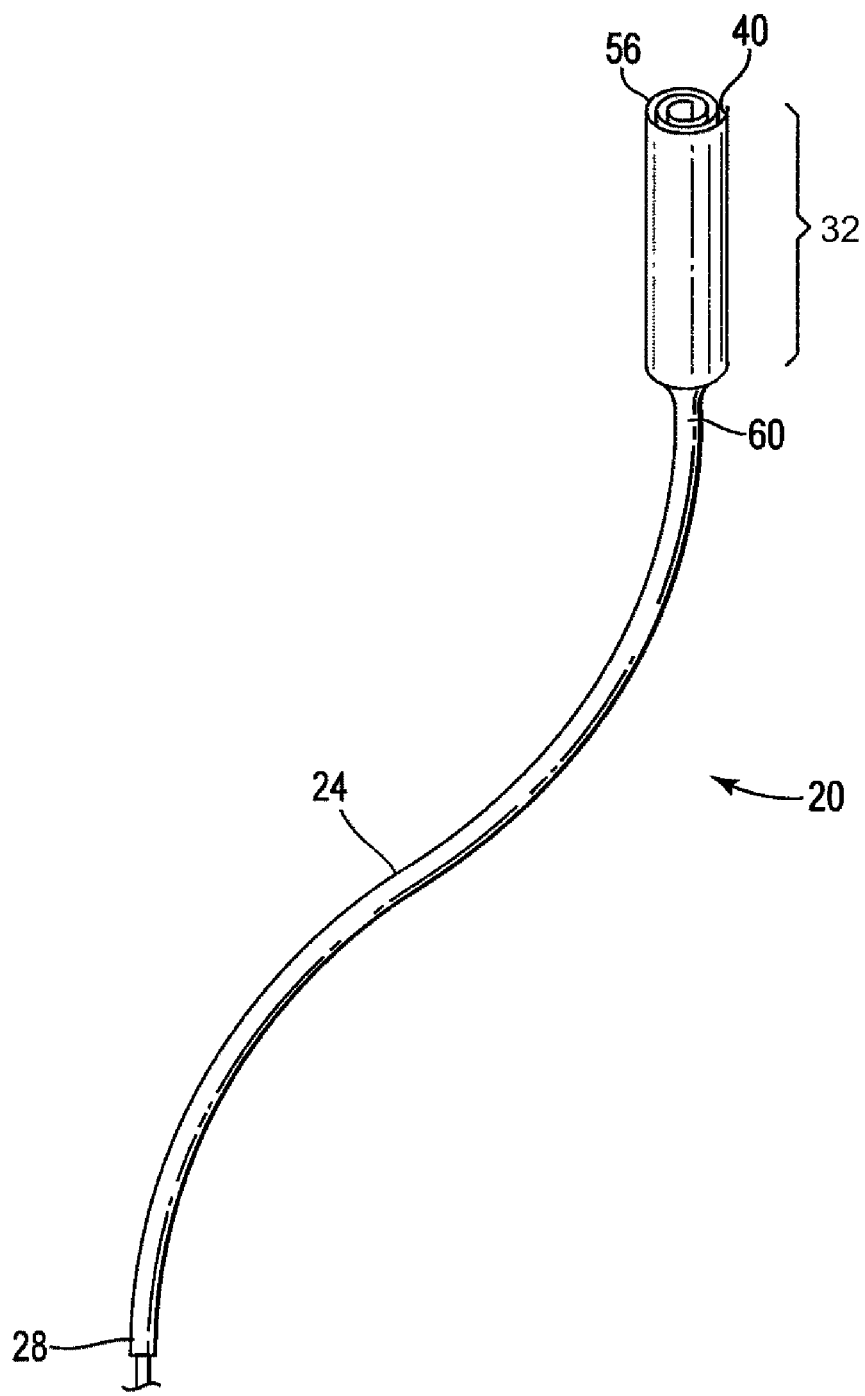

FIGS. 2A-2B and 3A-3B are schematic views of a medical electrical lead 20 adapted for delivery to and stimulation of the anterior cardiac plexus 10. Alternatively, the medical electrical lead 10 can be used to stimulate the posterior cardiac plexus. Other alternative stimulation sites within a patient's autonomic nervous system can include, but are not limited to, the following: the deep part of the cardiac plexus; the coronary plexuses; the celiac plexus; and the mesenteric plexus. As shown in FIGS. 2A and 3A, the lead 20 includes a lead body 24 having a proximal end 28 adapted to be connected to a pulse generator or other implantable medical device and a flexible distal portion 32.

The lead body 24 can have any appropriate configuration as is known in the art. The lead body 24 generally includes an outer insulation and one or more wires or conductors disposed therein. In one embodiment of the present invention, the lead body 24 has a co-radial design. Alternatively, the lead body 24 is co-axial. In yet a further embodiment of the present invention, the lead body 24 includes one or more lumens adapted to receive a guiding element such as a guidewire or a stylet.

The distal portion 32 of the lead 20 is flexible and is adapted to generally conform to the shape of the anatomical region to which it is deployed. According to one embodiment of the present invention, the distal portion 32 is generally adapted to conform to an aortic region and, more particularly, to the aortic arch 14 of a patient's anatomy. The distal portion 32 is made from silicone, polyurethane, another flexible biocompatible polymer, or a combination thereof, and, in one exemplary embodiment, has a thickness ranging from about 0.25 to about 4 mm. In an alternate exemplary embodiment, the distal portion 32 has a thickness ranging from about 0.25 to about 1 mm. The material composition and the thickness determine the general flexibility of the distal portion and its ability to conform to or wrap around a selected anatomical region or structure. Additionally, the distal portion 32 should be flexible enough to be furled or otherwise compacted such that the distal portion 32 can be delivered to the target stimulation site using a guide catheter or other delivery tool. According to a further exemplary embodiment of the present invention, the material of composition of the distal portion 32 should be sufficiently elastic such that it allows the distal portion to self-expand once the distal portion 32 has been delivered to the cardiac plexus 10. Alternatively, the distal portion 32 is configured such that it can be wrapped around an outer portion of a guide catheter or cannula. According to another embodiment of the present invention, the lead 20 including the distal portion 32 is adapted to be delivered to the cardiac plexus 10 using an endoscopic tool such as shown and described in co-owned and co-pending U.S. application Ser. No. 11/685,476, entitled "Method and Apparatus for Endoscopic Access to the Vagus Nerve," which is herein incorporated by reference.

Figure 4:
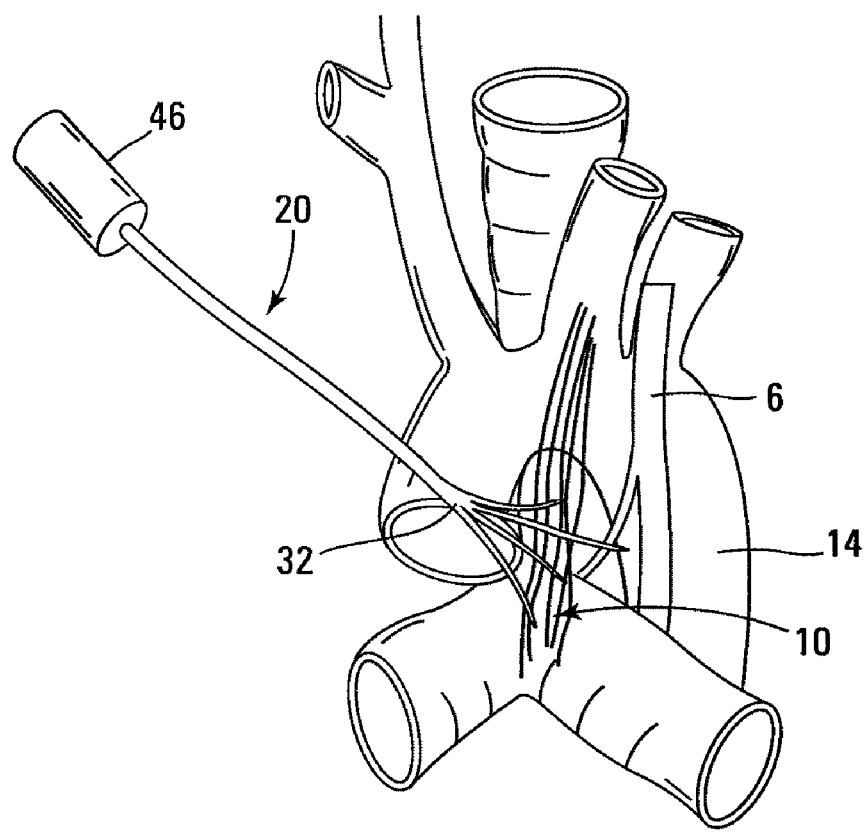
FIG. 4 is a close-up schematic view of a distal portion of a lead positioned adjacent the cardiac plexus according to one embodiment of the present invention.

According to one embodiment of the present invention, the distal portion 32 includes one or more elongate members 36, as shown in FIGS. 2A and 4. The one or more elongate members 36 have at least one generally planar surface and are sufficiently flexible enough to be furled together or otherwise compacted to fit within a guide catheter or other delivery tool, as mentioned above. According to another exemplary embodiment of the present invention, the one or more elongate members 36 are substantially cylindrical. Once deployed in a region of the cardiac plexus 10, the elongate members 36 are adapted to conform to a surface of the aortic arch 14, and more particularly, to a region of the aortic arch 14 generally associated with the cardiac plexus 10.

Alternatively, according to another embodiment of the present invention, the distal portion 32 is adapted such that the elongate member 36 or members can be interwoven through the nerves branches and/or ganglia in a region generally associated with the cardiac plexus 10, as shown in FIG. 4. According to this embodiment, the elongate member 36 or members includes one or more lumens adapted to receive a guidewire or other member for directing and guiding the elongate member(s) 36 through the nerve branches or ganglia to a target stimulation site.

Figure 5:
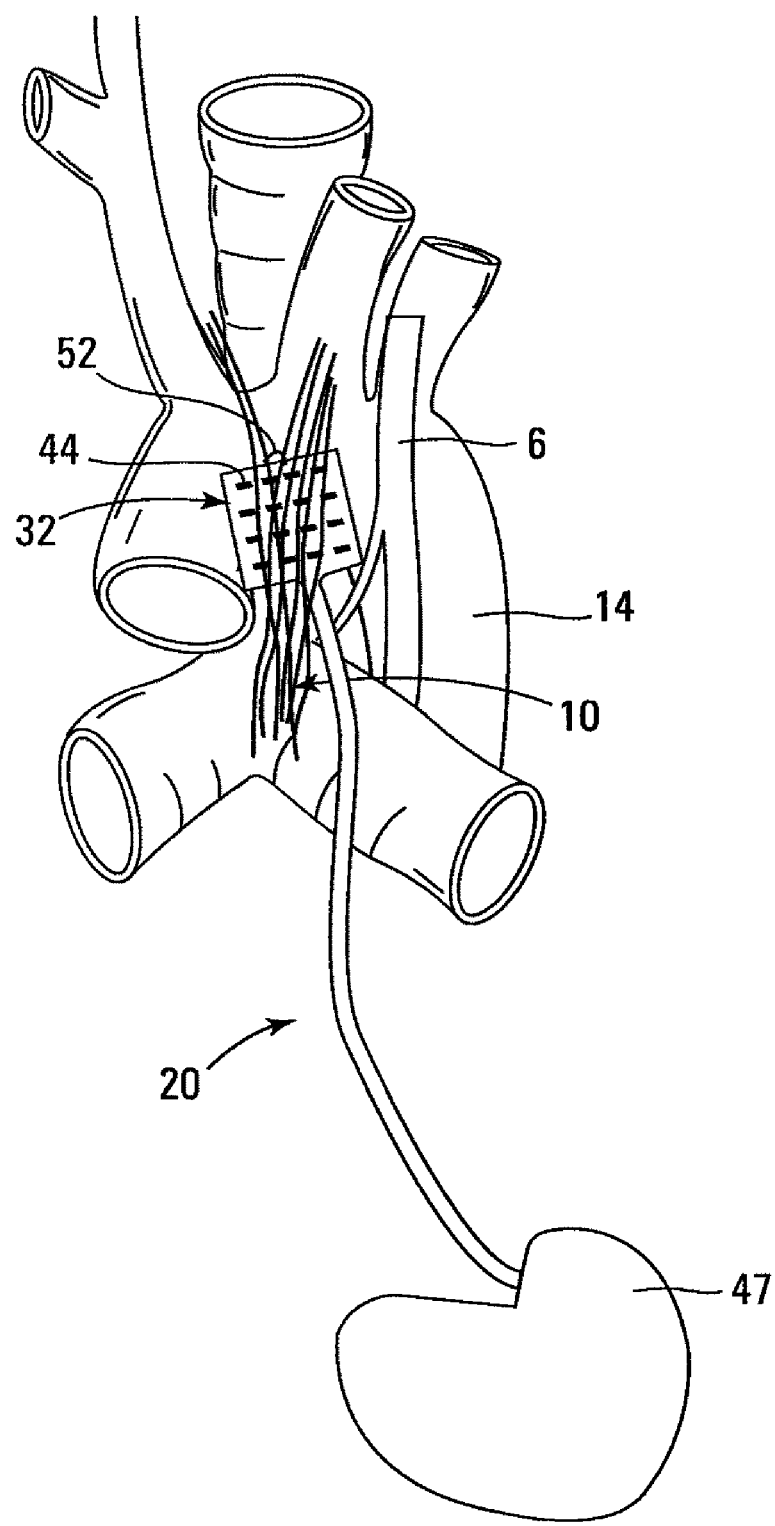
FIG. 5 is a close-up schematic view of a distal portion of a lead positioned adjacent the cardiac plexus according to another embodiment of the present invention.
Figure 6:
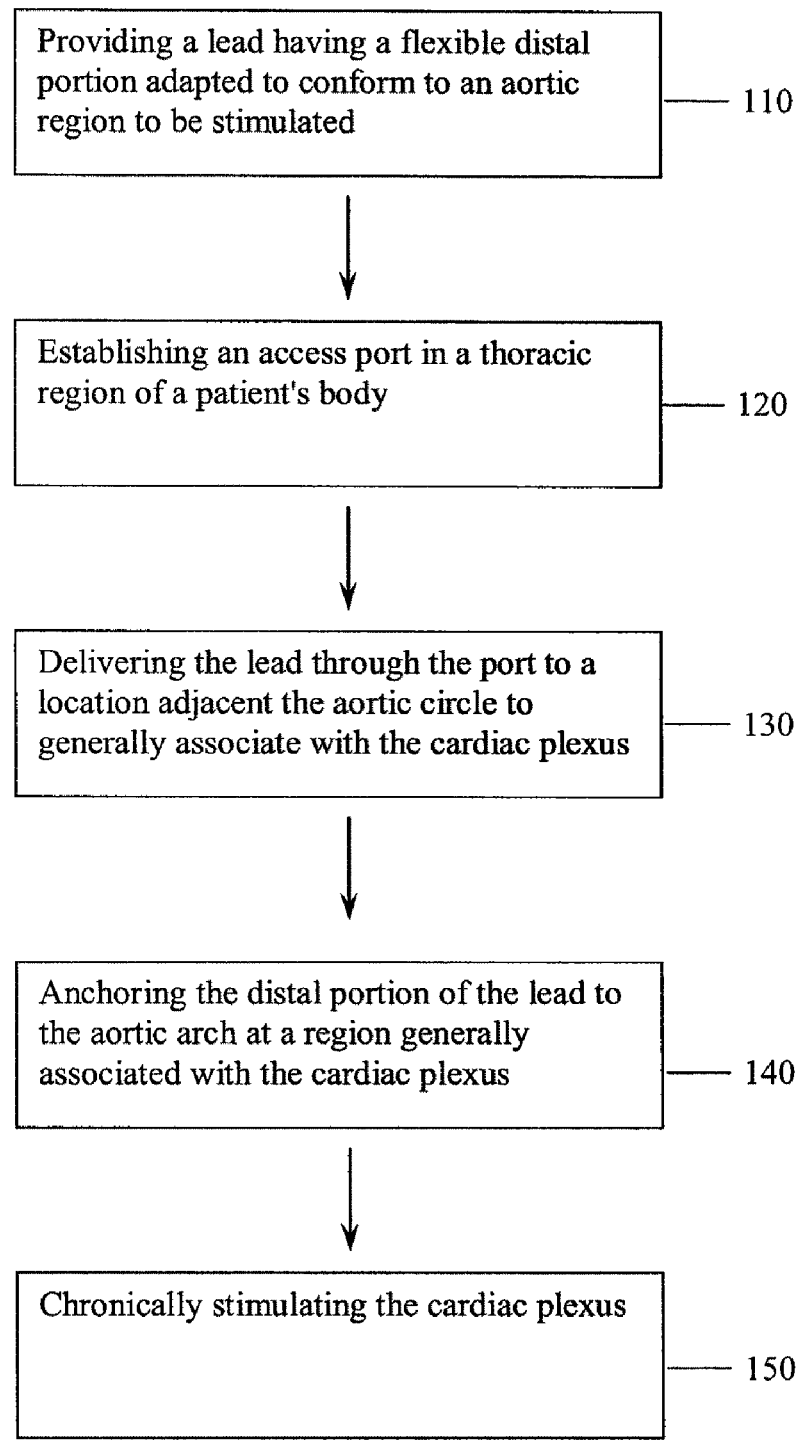
FIG. 6 is a flow chart of a method according to yet another embodiment of the present invention.

According to another embodiment of the present invention, the distal portion 32 includes a generally planar portion 40 having, for example, a generally square or rectangular shape, as shown in FIGS. 3A and 5. The generally planar portion 40 of the distal portion 32 is flexible enough such that it can be furled or rolled up to fit into a delivery catheter or other delivery tool. Once deployed to a location on the aorta 14 generally associated with the cardiac plexus 10, as shown in FIG. 5, the generally planar portion 40 is adapted to generally conform to a portion of an outer surface of the aortic arch 14, and more particularly, to a region of the aortic arch 14 generally associated with the cardiac plexus 10. According to a further embodiment of the present invention, the generally planar portion 40 is adapted to wrap around an outer surface of the aortic arch 14.

The distal portion 32 also includes a plurality of electrodes 44. At least one electrode 44 is adapted to deliver a stimulating pulse to the cardiac plexus 10. Additionally, one or more electrodes 44 can be a sensing electrode. According to one embodiment of the present invention, the electrodes 44 are individually addressable. Individually addressable electrodes 44 allow for flexibility in electrode selection, resulting in greater control over the current field and the direction of stimulation as well as allowing for multiple options for stimulation and sensing.

The electrodes 44 can be located on one or more of the elongate members 36, as shown in FIG. 2A. Alternatively, the electrodes 44 are located on the generally planar portion 40 of the distal portion 32, as shown in FIG. 3A. The electrodes 44 can be arranged on the distal portion 32 such that they form an electrode array. According to one embodiment of the present invention, the electrodes 44 can be arranged on the distal portion 32 such that they form a grid pattern. In one embodiment, a spacing between the individual electrodes ranges from about 100 to about 200 microns. An electrode array also allows for multiplexing to be performed at the stimulation site. Multiplexing occurs when multiple functions are being carried out at once within the same system. Additionally, an electrode array offers selective stimulation which offers the ability to perform electronic repositioning of the distal portion 32 of the lead 20.

According to a further embodiment of the present invention, a microstimulator 46 can be used to control the electrodes 44 located on the distal portion 32, as shown in FIG. 4. The microstimulator can either be embedded in the distal portion 32 or, alternatively, tethered to the distal portion 32. The microstimulator 46 can have any suitable design as is known to those of skill in the art. An exemplary microstimulator is shown and described in U.S. Pat. No. 5,324,316, which is herein incorporated by reference. Additionally, the microstimulator may include appropriate telemetry allowing for wireless communication with an internal or an external device. Alternatively, the electrodes 44 located on the distal portion 32 can be controlled using a conventional pulse generator 47 or other implantable medical device, as shown in FIG. 5.

As shown in FIGS. 2A and 3A, the distal portion 32 also includes one or more fixation regions 50 including one or more fixation members 52. Providing a plurality of fixation members 52 at a given location increases the stability of fixation should one or more fixation members 52 fail to engage the tissue at the target location (e.g. the outer surface of the aortic arch 14). According to one exemplary embodiment, at least one fixation member 52 is located at a distal end 56 of the distal portion 32. As shown in FIG. 2A, one elongate member 36 includes a distal fixation member 52. Alternatively, each elongate member 36 can include a fixation member 52 located at a distal end of the elongate member 36. According to another embodiment of the present invention, the distal portion 32 includes a first fixation member 52 located at a distal end 56 of the distal portion 32 and a second fixation member 52 located at a proximal end 60 of the distal portion 32.

According to one embodiment of the present invention, the fixation members 52 are small, if not tiny, tissue grasping hooks adapted to grasp the tissue on the outer surface of the aortic arch 14. The fixation members 52 take advantage of the flexibility of the distal portion such that when the distal fixation member is engaged the distal portion 32 of the lead 20 can be stretched such that tension is applied to the distal portion 32 allowing the second fixation member to easily engage the tissue at a second engagement site effectively securing the distal portion 32 of the lead at the stimulation site.

According to yet another embodiment, the present invention is a method of implanting a medical electrical lead 20 in a patient to stimulate the cardiac plexus 10, as shown in FIG. 5. First, a lead 20 having a flexible distal portion 32 adapted to conform to an aortic region 14 generally associated with the cardiac plexus 10 is provided (block 110). The distal portion 32 of the lead 20 is furled or otherwise compacted such that it can be inserted into a guide catheter or another delivery tool, such as a cannula. An access port is established in a thoracic region of a patient's body (block 120). Access to the cardiac plexus 10 can be achieved from either the right side or the left side of a patient's chest or from the xiphoid region. Using a subxiphoid approach, access to the aorta arch 14 can be achieved without a need for dropping the patient's lung. An endoscopic tool, as referenced above, can be used to identify and isolate the nerves forming the cardiac plexus 10. Electrodes adapted to acutely stimulate the nerves in the cardiac plexus 10 can be used to acutely stimulate the region to determine an optimal stimulation threshold as well as a region of the cardiac plexus 10 which produces a desired effect. Using visualization techniques well known in the art, the lead 20 of the present invention can then be inserted into the access port and delivered to the target stimulation site (block 130). The distal portion 32 of the lead 20 is then deployed from the guide catheter or cannula and anchored to a site on the aortic arch 14 generally associated with the cardiac plexus 10 (block 140). Anchoring the distal portion 32 of the lead 20 generally includes engaging a first, distal hook 52 located at the distal end 56 of the distal portion 32 to a site on the aorta, while a second, proximal hook 52, is still within the delivery tool. Tension is then applied to the distal portion 32 of the lead 20, stretching the distal portion 32 over the region of the aorta 14 generally associated with the cardiac plexus 10. Once sufficient tension has been applied to the distal portion 32, the second proximal fixation member 52 is deployed to engage the aorta 14 effectively anchoring the distal portion 32 of the lead 20 at a region of the aorta 14 generally associated with the cardiac plexus 10. Alternatively, the elongate members 36 can be interwoven through the nerves branches and/or ganglia in a region generally associated with the cardiac plexus 10, as best shown in FIG. 4, securing the distal portion 32 of the lead 20 without the need for additional fixation members 52. Once secured, the electrodes 44 located on the distal portion can then be used to deliver chronic stimulation to the cardiac plexus 10 (block 150).

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method of implanting a medical electrical lead in a patient for stimulating a patient's cardiac plexus, the method comprising:

establishing an access port in a thoracic region of a patient's body;

delivering a medical electrical lead through the port to a region located on an external surface of the aortic arch at the location generally associated with the cardiac plexus, the lead including one or more conductors extending within a lead body having a longitudinal axis and including a flexible distal portion adapted to be stretched such that tension can be applied to the distal portion along the longitudinal axis of the lead body, the distal portion comprising a generally planar surface configured to conform to and wrap around the external surface of a patient's aortic arch at a region of the aorta generally associated with the cardiac plexus; at least one fixation member adapted to engage the external surface of the aortic arch; and at least two electrodes located on the generally planar surface of the flexible distal portion, the electrodes adapted to deliver an electrical pulse to the cardiac plexus;

transitioning the flexible distal portion of the lead from a compact configuration suitable for delivery to a non-compact configuration suitable for contact with the external surface of the aortic arch;

anchoring the distal portion of the lead to the external surface of the aortic arch at the location generally associated with the cardiac plexus, wherein the step of anchoring the distal portion comprises stretching the distal portion of the lead in a direction along the longitudinal axis of the lead body such that the distal portion contacts and wraps around the external surface of the aortic arch generally associated with the cardiac plexus; and chronically stimulating the cardiac plexus.

2. The method according to claim 1, wherein the step of anchoring the distal portion further comprises:

engaging a first hook located on a distal end of the generally planar surface;

applying tension to the distal portion of the lead; and engaging a second hook located on a proximal end of the generally planar surface.

3. The method according to claim 1, further comprising: identifying and isolating the cardiac plexus.

4. The method according to claim 1, further comprising: acutely stimulating the cardiac plexus to determine an optimal stimulation threshold.

\* \* \* \* \*